United States Patent [19]

Colas et al.

[11] Patent Number: 4,912,241

[45] Date of Patent: Mar. 27, 1990

[54] ORGANOSILICON COMPOUNDS

[75] Inventors: André R. L. Colas, Glashutten, Fed. Rep. of Germany; Stephen E. Cray, South Glamorgan, Wales; Georg Frater, Uster, Switzerland

[73] Assignee: Dow Corning Limited, Barry, Wales

[21] Appl. No.: 226,326

[22] Filed: Jul. 29, 1988

[30] Foreign Application Priority Data

Jul. 31, 1987 [GB] United Kingdom .................. 8718140

[51] Int. Cl.$^4$ ............................................. C07F 7/06
[52] U.S. Cl. .................................. 556/439; 556/441
[58] Field of Search ........................ 556/438, 439, 441

[56] References Cited

U.S. PATENT DOCUMENTS 4,562,278 12/1985 Hill ..................................... 556/418

FOREIGN PATENT DOCUMENTS 0138590 4/1985 European Pat. Off. .

Primary Examiner—Robert L. Stoll
Assistant Examiner—Stuart L. Hendrickson
Attorney, Agent, or Firm—Marc C. Pawl; Robert L. McKellar

[57] ABSTRACT

Organosilicon compounds having at least one unit of the general formula

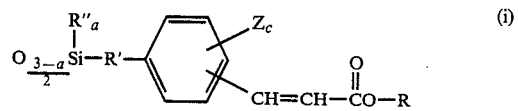

in which R represents alkyl, R' is a divalent alkylene, oxyalkylene, alkenylene or oxyalkenylene, Z represents an alkyl, alkoxy or hydroxyl group, a has a value of 0, 1, 2 or 3 and c is 0 to 1, wherein at least one of Z and R' is linked to the multivalent aryl group via an ether linkage, are useful for absorbing UV radiation. Especially if polymeric (with e.g. diorganosiloxane units) they can be incorporated in sunscreen preparations to improve their substantivity to the skin. A process for preparing the compounds is also disclosed.

9 Claims, No Drawings

ORGANOSILICON COMPOUNDS

This invention is concerned with novel organosilicon compounds which are effective in absorbing ultra violet radiation.

A number of organic compounds, generally organic acids and derivatives thereof, are known to be chromophores having U.V.-absorbing properties and are employed on a commercial scale as ingredients in sunscreen preparations or as plastic additives. Although such materials function adequately they are easily removed from the substrate to which they have been applied. For example, cosmetic sunscreen preparations can be removed during bathing thus requiring repeated applications if protection is to be maintained. It is also desirable that the active ingredient remain on the surface of the skin rather than be absorbed thereby.

Compounds which overcome this problem to a certain extent are disclosed for example in European Patent Specification 138 590, which provides organosilicon compounds which are silanes represented by the general formula

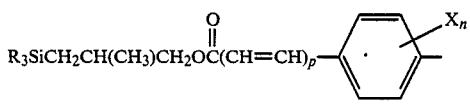

or siloxanes having at least one unit represented by the general formula

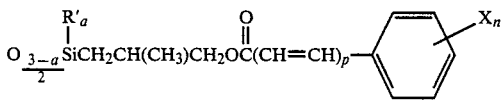

any other units present in the said siloxanes being those represented by the general formula

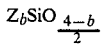

wherein each R represents a halogen atom, an alkyl group having from 1 to 4 carbon atoms or a phenyl group, an alkoxy group having less than 8 carbon atoms or an alkoxyalkoxy group having less than 8 carbon atoms, R' represents an alkoxy group having less than 8 carbon atoms, an alkoxyalkoxy group having less than 8 carbon atoms, a methyl group or a phenyl group, X represents a hydroxyl group, methoxy group or ethoxy group when p=1 or a hydroxyl group or —NQ$_2$ group, in which each Q is lower alkyl, when p=0, Z represents a hydrogen atom, a monovalent hydrocarbon group or a monovalent halogenated hydrocarbon group, a is 0, 1 or 2, b is 0, 1, 2 or 3, n is 0 or 1 and p is 0 or 1. These siloxane materials may be prepared e.g. by the reaction of inter alia an allyl ester of certain cinnamates with a hydrosiloxane polymer, i.e. a polymer having silicon-bonded hydrogen atoms.

It was found, however, that the materials thus obtained were susceptible to hydrolysis at the ester linkage, for example by enzymatic hydrolysis on the skin when these materials were used as cosmetic sunscreen agents. As a result of such hydrolysis the chromophore portion of the molecule would no longer be substantive and could easily be washed off or could penetrate the skin. It was also found that purification of the reaction product by removal of unwanted starting material was very difficult.

The present invention is concerned with novel organosilicon compounds which are more stable to hydrolysis than the aforementioned prior art organosilicon compounds and which can be obtained in a more pure state.

The invention accordingly provides novel organosilicon compounds having at least one unit of the general formula

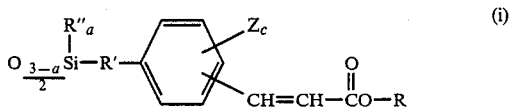

any other units present in the said siloxanes being those represented by the general formula

in which general formulae R represents an alkyl group having up to about 18 carbon atoms, R' is a divalent alkylene or oxyalkylene group having from 2 to about 20 carbon atoms, or a divalent alkenylene or oxyalkenylene group having from 2 to 20 carbon atoms, wherein the carbon-carbon double bond is adjacent to the silicon atom, R" represents a halogen atom, an alkyl, aryl, alkoxy or alkoxyalkoxy group having less than 9 carbon atoms, Q represents a hydrogen atom, a monovalent hydrocarbon group or a monovalent halogenated hydrocarbon group having less than 19 carbon atoms, Z represents an alkyl or an alkoxy group having from 1 to 8 carbon atoms or a hydroxyl group, a and b each have a value of 0, 1, 2 or 3 and c is 0 or 1, provided that at least one of Z and R' is linked to the multivalent aryl group via an ether linkage.

In the general formula of the organosilicon compounds of the invention R may be for example methyl, butyl or dodecyl; R' may be trimethylene, methyldimethylene, butylene, isobutylene, oxytrimethylene, oxyisobutylene, propenylene, octenylene, oxypropenylene or oxyhexenylene, but preferably R' has 3 or 4 carbon atoms; each R" may independently be e.g. methyl, ethyl, phenyl, methoxy, methoxyethoxy, but preferably at least 80% of all R" groups are methyl groups; each of the Q substituents may be hydrogen or a monovalent hydrocarbon or halogenated hydrocarbon group, preferably having less than 8 carbon atoms, for example methyl, vinyl, phenyl and 3,3,3-trifluoropropyl; Z, if present may be for example methyl, propoxy, hydroxy and is preferably methoxy or ethoxy; a is preferably 1, while b is preferably 2, making the organosilicon compound a substantially linear polyorganosiloxane polymer.

The preferred organosilicon compounds are those wherein the substituent —CH=CH—C(O)O—R in units (i) occupies the para-position in relation to another substituent which is linked to the —(C$_6$H$_{4-c}$)— group via an ether linkage. Such organosilicon compounds are therefore those having at least one unit of the general formula

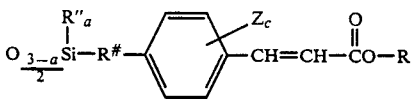

or of the general formula

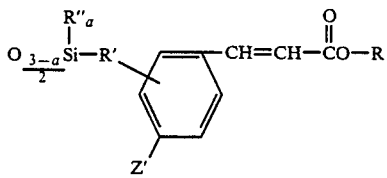

in which R, R', R", Z, a and c are as defined above, R# represents a divalent oxyalkylene or oxyalkenylene group having from 2 to 20 carbon atoms linked to —($C_6H_{4-c}$)— via the oxygen atom, the carbon-carbon double bond in the oxyalkenylene group being adjacent to the silicon atom and Z' represents a hydroxyl group or an alkoxy group having from 1 to 8 carbon atoms. The preferred organosilicon compounds are effective in absorbing ultra violet radiation in the erythemic region (290-320 nm) which makes them particularly suitable for use in cosmetic sunscreen preparations, where absorption in the UV-B region is particularly desirable. Most preferred for this application are those that have a maximum absorbance at 300-320 nm.

The organosilicon compounds of the present invention have at least one unit falling within the general formula (i). Particularly preferred organosilicon compounds are polymeric materials. They may be homopolymers consisting only of such units (i) or they may be copolymers containing both units (i) and units having the general formula (ii). The organosilicon compounds may vary from freely flowing liquids to highly viscous gum like materials or resinous solids. Preferred, at least for cosmetic applications, are the liquid substantially linear organosiloxane homopolymers and copolymers. It is also preferred for such applications that at least 30% and preferably 80% of the total R" and Q substituents are methyl groups.

Organosilicon compounds of the invention which are especially preferred, are those wherein the number of units (i) is restricted to a maximum of 20% of the total number of siloxane units in the molecule. These especially preferred organosilicon compounds exhibit an improved stability to ultra violet radiation. It has been found that when this proportion exceeds about 20% the ultra violet absorption effect, although being very high initially, decreases with time. While we do not wish to be bound by a theory it is believed that this decrease is due to an intramolecular addition reaction between two vinylene groups of adjacent chromophore substituents. Especially in such applications as sunscreen preparations a long term stability of the UV absorption capability is desirable. The especially preferred organosilicon compounds of the present invention have in the molecule at least one unit falling within the general formula (i), most preferably within the general formulae (iii) or (iv). A maximum of 20% of the total number of siloxane units of these especially preferred organosilicon compounds may have a structure represented by formula (i). For maximum retention of the U.V. absorbing property with time it is preferred that the number of units (i) be limited to 10% or less of the total, especially where these units are distributed randomly in an organosiloxane polymer. However, units of the general formula (i) are preferably situated at the end of the organosiloxane polymer forming one or more endblocking units of the polymer. In the most preferred organosilicon compounds which are substantially linear polyorganosiloxane polymers, both end blocking units have a structure represented by the general formula (i), while all other units are according to the general formula (ii). The most preferred organosilicon compounds have a relatively large number of units according to the general formula (ii). Particularly useful are those organosilicon compounds having the general formula (iii)-(ii)$_x$-(iii) or (iv)-(ii)$_x$-(iv) wherein a in (iii) or (iv) equals 1 and b in (ii) equals 2, and wherein x has a value of at least 9, preferably 98 or more.

The organosilicon compounds of the present invention can be prepared by the reaction of an organosilicon compound having a silicon-bonded hydrogen atom, with an alkyl ester of certain cinnamic acid derivatives. This invention therefore also includes a process for the preparation of organosilicon compounds of the kind specified herein, which comprises reacting together (A) a compound of the general formula

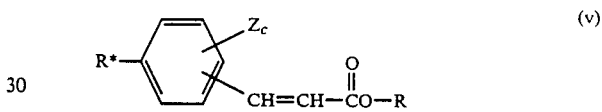

wherein R, Z and c are as defined above, R* is an alkenyl, oxyalkenyl, alkynyl or oxyalkynyl group having from 2 to about 20 carbon atoms, wherein the carbon-carbon unsaturated bond is at the free end of the R* group, and wherein at least one of R* and Z is linked to the —($C_6H_{4-c}$)— group via an ether linkage, and (B) an organosilicon compound having at least one unit of the general formula

any other units present in the organosilicon compounds being those represented by the general formula

wherein R", Q, a and b are as hereinabove defined.

In the general formula (v) R* is the monovalent unsaturated or further unsaturated group corresponding to R' of formula (i) and may be for example methylallyl, oxymethyallyl, propargyl, oxypropargyl, allyl, hexenyl or oxyoctenyl. Preferably R* has acetylenic unsaturation between the first two carbon atoms.

The reaction is preferably carried out employing stoichiometric proportions of (A) and (B) or a slight stoichiometric excess of (A). However, a stoichiometric deficiency of (A) can be employed if residual silicon-bonded hydrogen is desired in the product.

Preferred organosilicon compounds of the invention, which have at least one unit according to the general formula (iii) or (iv), may be prepared by reacting (A) compounds of the respective general formulae

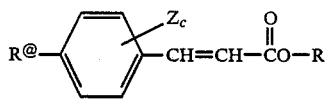

or

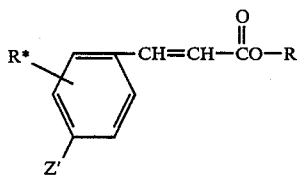

wherein R, R*, Z, Z' and c are as defined above and R@ represents an oxyalkenyl or oxyalkynyl group having from 2 to 20 carbon atoms linked to —(C₆H₄₋c)— via the oxygen atom, the carbon-carbon unsaturated bond being at the free end, with organosilicon compounds (B).

In order to prepare the particularly preferred polymeric organosilicon compounds of the invention, compounds of the general formula (v) may be reacted with organosilicon compounds (B) which are themselves polyorganosiloxanes having at least one unit of the general formula (vi), the other units present having the general formula (ii). Alternatively polymeric organosilicon compounds of the invention can also be obtained by first preparing the corresponding hydrolysable silane, employing in place of (B) the corresponding SiH containing silane (C) which has the general formula

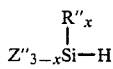 (viii)

wherein R" is as defined above, Z" is a hydrolysable group, preferably alkoxy having 1 to 8 carbon atoms and x has a value of 0, 1 or 2. The silane (D) resulting from this reaction may be submitted thereafter to cohydrolysis or equilibration with (E) cyclic or (F) linear polyorganosiloxanes consisting essentially of units of the formula (ii). Silanes (D) which can be used in this method are novel in themselves and are included in the scope of the present invention. Silanes (D) have the general formula

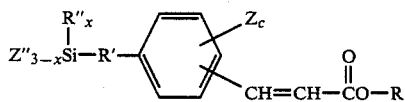 (vii)

wherein R, R', R", Z, Z", x and c are as defined above. When using this process to prepare polymeric versions of the preferred organosilicon compounds of the invention, i.e. those having at least one unit of the general formula (iii) or (iv) preferred silanes (D) are used which have respectively the general formula

 (vii')

or

-continued

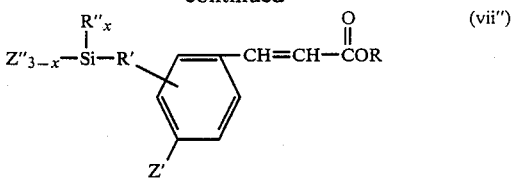 (vii")

In order to obtain the particularly preferred polymeric organosilicon compounds of the invention, the reaction is carried out in such a way that in the reaction product at least one siloxane unit and no more than 20% of the total number of siloxane units has a structure according to formula (i). This may be achieved by reacting polymeric organosilicon compounds (B), which have a maximum of 20 mole % silicon-bonded hydrogen atoms, with stoichiometric amounts of compound (A). Excess amounts of (A) may also be used in this case. If residual SiH groups are desired in the organosilicon compound product less than stoichiometric amounts of compound (A) may be employed. The organosilicon compounds of the invention may also be obtained by reacting polymeric organosilicon compounds (B) having more than 20 mole % silicon-bonded hydrogen atoms, with less than stoichiometric amounts of compound (A). Most preferably, however, organosilicon compounds (B) are employed which are polydiorganosiloxanes endblocked with diorganohydrosiloxane units provided the siloxane has a minimum chain length of 10 silicon atoms.

The reaction between (A) and (B) may be carried out employing known procedures for the addition of silicon-bonded hydrogen atoms to groups containing aliphatic unsaturation. Thus, such reactions are generally catalysed by a platinum group metal or a compound or complex of such a metal. Examples of catalysts which may be employed in the reaction (A) and (B) are platinum on carbon, chloroplatinic acid, platinum acetyl acetonate, complexes of platinum compounds with unsaturated compounds e.g. olefins and vinyl siloxanes, complexes of rhodium and palladium compounds and complexes of platinum compounds supported on inorganic substrates. The addition reaction may be performed at reduced, atmospheric or increased pressure. It is generally preferred to employ a solvent e.g. toluene or xylene in the reaction mixture although the presence of a solvent is not essential. It is also preferred to carry the reaction out at elevated reaction temperatures e.g. from about 50° C. up to the reflux temperature of the reaction mixture.

In contrast to the organosilicon compounds of the prior art referred to hereinabove the organosilicon compounds of this invention have no ester or other hydrolysable group present between the silicon atoms and the active chromophore group. They are thus better adapted for use under conditions conducive to hydrolysis for example when incorporated in cosmetic sunscreen preparations. The organosilicon compounds of the invention are also less soluble in most solvents than the compounds of the above mentioned prior art while the unreacted compounds (A) remain soluble in said solvents. This is particularly true for the polymeric organosilicon compounds of the invention. This facilitates separation of the organosilicon compounds from unreacted compounds (A). Purer products are therefore obtainable making the materials especially useful for incorporation in cosmetic sunscreen preparations.

When preferred compounds (A), having acetylenic unsaturation at the ree end of the R* group, are used for making the organosilicon compounds of the invention the yield of desired product is greatly improved as a result of a substantially complete addition of compound (A) to the reactant (B). This in turn reduces the need for purification of the reaction product.

The organosilicon compounds of this invention have similar UV absorbence characteristics to those disclosed in European Patent Specification 138 590. They are useful as agents for preventing sunburn. They may be applied per se to the skin but are more preferably formulated into compositions with, for example, inert carriers e.g. solvents such as ethanol, isopropanol, glycerine and mineral oil and cream base materials such as stearic acid, propylene glycol, beeswax and cetyl alcohol. Other conventional ingredients e.g. perfumes and known U.V. absorbing substances may also be included in the formulated compositions. The organosilicon compounds of the present invention are also useful in the coating of substrates e.g. wood, plastics or metal, to which they may be applied either per se or as additives to coating compositions or they may be incorporated as additives in plastics materials.

The following examples, in which parts and percentages are expressed by weight, Me denotes a methyl group and Bu denotes a butyl group, illustrate the invention.

The following examples, in which parts and percentages are expressed by weight, Me denotes a methyl group and Bu denotes a butyl group, illustrate the invention.

Preparation of Cinnamate Esters p-Hydroxy Cinnamic Acid n-Butyl Ester 335 g (2.0M) of p-hydroxy cinnamic acid (commercial product; 98% purity, origin: Fluka, Buchs, Switzerland) are dissolved in 800 ml (645 g, 8.7M) n-butanol. 1 liter of cyclohexane and 10 g of p-toluene sulfonic acid are added. The mixture is heated to reflux (temperature of the mixture 80°–82° C.) and the water formed is collected in a water trap. When no more water is entrained (after 24–27 hours) the mixture is cooled to room temperature, extracted twice with a 5% aqueous solution of sodium hydrogencarbonate followed by two washings with water. The organic extract is evaporated in vacuo (about 12 mbar) at about 45° C. until a crystalline mass is formed. Residual n-butanol is distilled off in high vacuo (about 0.1 mbar) at 45° C. The coloured crystalline residue (about 500 g to 550 g) is taken up in 100 ml pentane and filtered via a Buchner funnel. The almost colourless crystals (small prisms) are dried in high vacuo (about 0.1 mbar) at 50° C. (about 6 hours). 373.6 g of product melting at 72° to 74° C. are obtained. Another 44.3 g of product may be obtained from the mother liquors. Recrystallization of a sample of this product from hexane gave colourless prisms, mp 77.5°–79° C. Yield 417.9 g (94.8% of theory) of p-hydroxy cinnamic acid n-butyl ester.

3-[4-(2-Propinyl)Oxy-Phenyl]-2-Propenoic Acid n-Butyl Ester 903 g (4.1M) of p-hydroxy cinnamic acid n-butyl ester (see above) are dissolved in 4 liter acetone. 622 g (4.5M) of finely powdered potassium carbonate and 523.5 g (4.4M) freshly distilled butinyl bromide are added. Under stirring the suspension is heated to reflux (temperature in the mixture 56° C.). After refluxing for about 18 hours the starting material is consumed. The yellow suspension is cooled to about 10° C. and filtered. The filtrate is evaporated to dryness in vacuo (about 12 mbar) at 35° C. The yellow oily residue is added with stirring to about 6 liters of water. A white crystalline precipitate is obtained which is isolated by filtration. The solid material is washed with water and dried. It is crystallised from 1 liter of hexane. The product, 805.5 g, is obtained in colourless prisms, mp 38.5° to 39.0° C. From the mother liquor another 183.0 g of product could be isolated. Total yield 988.5 g (93.3% of theory).

3-[4-(2-Methyl-2-Propenyl)Oxy-Phenyl]-2-Propenoic Acid n-Butyl Ester 121 g (0.88M) of finely powdered potassium carbon are are introduced into 400 ml N,N-dimethyl formamide. With stirring 1 g of potassium iodide, 176 g (0.8M) of p-hydroxy cinnamic acid n-butylester (see above) and 85 ml (0.87M) of methallyl chloride are added. Under a blanket of nitrogen and with stirring the mixture is heated up to 70° C. and kept at that temperature until the starting material is consumed (about 21 hours). The mixture is cooled to room temperature and 500 ml of water are added. The solution is extracted three times with a total of 1.2 liter of hexane and the hexane extracts are subsequently washed with a 10% solution of sodium carbonate and water. The hexane extract is evaporated at 30° C. in vacuo (about 12 mbar) to dryness. The residue is crystallised from 80 ml of methanol at 0° C. The colourless crystalline product is collected by filtration and dried in high vacuo (about 0.1 mbar) at room temperature. 163.5 g (74.5% of theory) of product melting at 32°–33° C. are obtained.

3-[3-(2-Methyl-2-Propenyl)-4-Methoxy-Phenyl]-2-Propenoic Acid n-Butyl Ester 164.6 g (0.6M) of p-methallyloxy cinnamic acid n-butyl ester (see above) are dissolved in 450 ml N,N-dimethyl aniline and refluxed (pot temperature 198° C.) until the starting material is converted (about 18 hours). After cooling to room temperature the reaction mixture is diluted with 500 ml ether and extracted with 2N aqueous sulphuric acid solution several times until the N,N-dimethyl aniline is removed. The etheral solution is washed with water until neutral.

From the etheral extract the intermediate 3-[4-hydroxy-3-(2-methyl-2-propenyl)phenyl]-2-propenoic acid n-butyl ester may be isolated by extraction with a 5% aqueous sodium hydroxide solution followed by acidification, extraction with ether, and column chromatography (silica gel, methylene chloride). The pure phenolic intermediate is a colourless crystalline substance mp 52°–53° C.

For the preparation of the title compound the etheral solution mentioned above is added to 330 g of a 10% aqueous sodium hydroxide solution containing 2 g of a phase transfer catalyst (e.g. Aliquat 336). With stirring and occasional cooling to keep the temperature around 25° C. 100 ml (0.6M) of dimethyl sulphate are added dropwise during about 1.5 hours. Stirring is continued for another 0.5 hour to complete the reaction. The ether layer is separated, washed with a 2.5% aqueous ammonia solution followed by a washing with water and evaporated to dryness in vacuo (about 12 mbar). The residue is a yellow oil, 148 g. This residue is fractionated in high vacuo (0.06 mbar) via a 30 cm-Widmer column giving 103.6 g (59.9% of theory) of an almost colourless liquid, $n_D^{20}$ 1,559–1560, bp 156° to 160° C. (0.06 mbar).

EXAMPLE 1

5.48 g of methyl 2-allyloxy n-butyl cinnamate ester (0.02 mole) were dissolved in 15 g of toluene and heated under nitrogen to about 80° C. 7.26 g of a hydrosiloxane (0.01 mole), having a degree of polymerisation of 10 and 20 mpc SiH groups, were then dissolved in about 10 g of toluene. A platinum complex was added to the ester over 60 seconds to give $10^{-4}$ mole of Pt per mole of SiH of the hydrosiloxane and the mixture was heated to 110°–115° C. Then the hydrosiloxane solution was added over a period of 30 minutes. The mixture was maintained at about 110° C. for a further 2 hours before it was allowed to cool to room temperature. The toluene was then evaporated to leave a residual oil, which was washed three times with methanol, to yield a cinnamate functional polymer having the following average structure, wherein x was not exactly defined but has an estimated value less than 0.5:

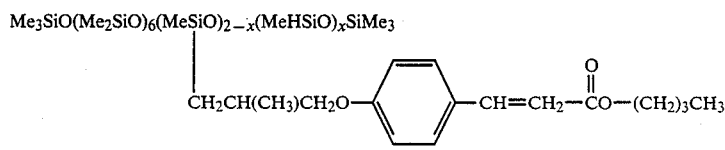

EXAMPLE 2

A reaction was carried out as in Example 1 except that instead of 5.48 g of methyl 2-allyl n-butyl cinnamate ester, 5.16 g of propargyloxy n-butyl cinnamate ester was used. The polysiloxane obtained had the average structure wherein x is as for Example 1

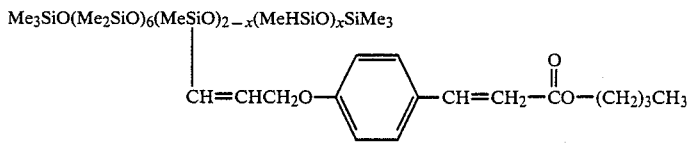

EXAMPLE 3

7.5 g of n-butyl ester of m-methallyl p-methoxy cinnamic acid (26 mmole) were mixed with 9.4 g (13 mmole) of a hydrosiloxane as described in Example 1 and 30 g of toluene. The mixture was heated with stirring to reflux under nitrogen. $2.4 \times 10^{-3}$ mmole of a platinum complex were added to the mixture and the reaction was carried out at 100°–110° C. for about 8 hours. Progress of the reaction was followed by measuring the SiH infrared absorption spectrum. After 8 hours 3 g (26 mmole) of 1-octene were added to remove all residual SiH in the mixture. After a further hour the mixture was allowed to cool to room temperature when residual toluene and 1-octene were evaporated leaving an oil. The polymer was washed with methanol and yielded a cinnamate functional siloxane having the following average structure

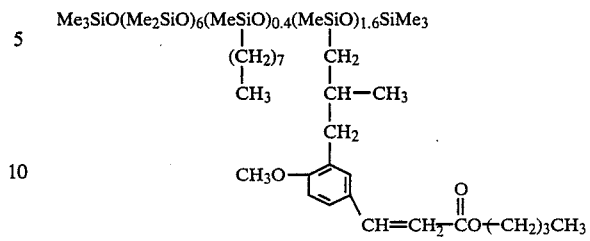

EXAMPLE 4

12.89 g of n-butyl ester of p-propynoxycinnamate were mixed with 18.6 g of a hydrosiloxane having the average formula

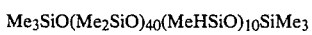

and 70 ml of toluene. The mixture was heated with stirring to reflux under nitrogen. About $4.5 \times 10^{-3}$ mmol of a platinum containing catalyst were added to the mixture which was kept at reflux temperarure for 4.5 hours. The progress of the reaction was followed by measuring the reduction of the SiH band in the infrared absorption spectrum. Then the reaction mixture was allowed to cool and toluene was evaporated under reduced pressure. The polymer was washed with $3 \times 25$ ml of methanol and 27 g of a cinnamate functional siloxane was obtained, which contained less than 1% of unreacted cinnamate ester. The siloxane has the average structure.

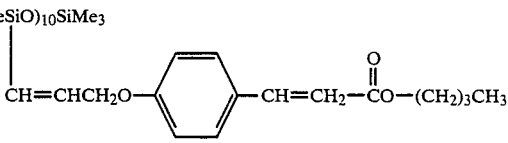

EXAMPLE 5

7.5 g of n-butyl ester of m-methallyl p-methoxy cinnamic acid (26 mmole) were mixed with 9.5 g of a hydrosiloxane as described in Example 4, and 30 g of toluene. The mixture was heated with stirring to reflux under nitrogen. $2.4 \times 10^{-3}$ mmole of a platinum complex were added to the mixture and the reaction was carried out at 100°–112° C. for about 5 hours. Progress of the reaction was followed by measuring the SiH infrared absorption spectrum. After 5 hours 4 g (26 mmole) of 1-octene were added to remove all residual SiH in the mixture. After a further 1.5 hours the mixture was allowed to cool to room temperature when residual toluene and 1-octene were evaporated to leave an oil. The polymer was washed with methanol and yielded 13.88 g of a cinnamate functional siloxane containing less than 1% of unreacted cinnamate ester having the following average structure

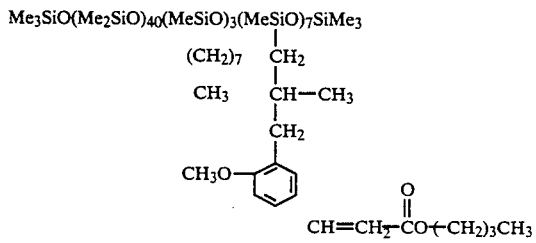

EXAMPLE 6

12.89 g of propargyloxy n-butyl cinnamate ester, 18.6 g of a hydrosiloxane copolymer of the average formula $Me_3SiO(Me_2SiO)_{40}(MeHSiO)_{10}SiMe_3$ and 70 ml of toluene were added to a 3-necked flask, equipped with a condenser, thermometer probe, stirrer and nitrogen blanket. The mixture was heated to about 100° C. after which 0.15 g of a platinum containing complex was added. The reaction mixture was refluxed for approximately 4.5 hours and then allowed to cool. The solvent was removed by evaporation under reduced pressure and 30.4 g of a residual oily substance was left. This residue was washed three times with 25 ml of methanol. 27 g of a product was retained which showed in HPLC analysis that about 1% unreacted cinnamate ester remained in the final product, which had the average formula

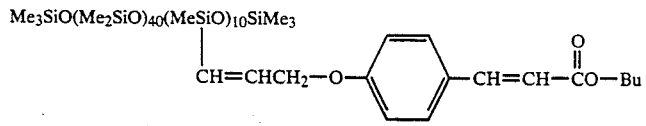

EXAMPLES 7-10

Zg of propargyl n-butyl cinnamate ester was added to a flask together with Y g of a hydrosiloxy-endblocked polydimethylsiloxane of the general formula $HMe_2SiO(Me_2SiO)_xSiMe_2H$ and about 30 ml of toluene as a solvent. The process was continued as in Example 6 using the same amount of platinum containing catalyst in all but Example 10, where only half the amount was used. The values for Z, Y, x and the yield of the reaction is shown in the Table below. The product has the average formula $RMe_2SiO(Me_2SiO)_xSiMe_2R$ in which R has the formula

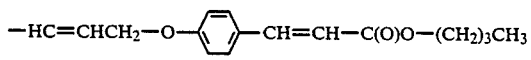

TABLE I

| Example | Z | Y | x | yield |
|---|---|---|---|---|
| 7 | 5.16 | 8.74 | 10 | 9.37 g |
| 8 | 5.16 | 14.80 | 18.2 | 16.16 g |

TABLE I-continued

| Example | Z | Y | x | yield |
|---|---|---|---|---|
| 9 | 6.16 | 36.86 | 39 | 39.15 g |
| 10 | 2.58 | 111.67 | 300 | 101.00 g |

EXAMPLE 11

5.16 g of propargyl n-butyl cinnamate ester (0.02 mole), 7.39 g of a hydrogendimethylsiloxane endblocked dimethylpolysiloxane having on average 120 siloxane units (0.015 mole) and 20 ml of toluene were added to a flask equipped with a condenser, thermometer probe, stirrer and nitrogen blanket. The mixture was heated to 100° C. when 60 microl of a platinum containing complex was added. The reaction mixture was allowed to reflux for approximately 6 hours and then allowed to cool. After evaporation of the solvent an oil was obtained which was washed with 3×75 ml of methanol. Analysis showed a 96% reaction yielding 67.9 g of product of the general formula

wherein Ar denotes

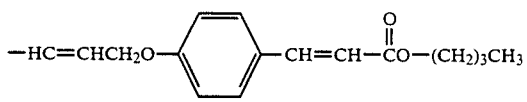

EXAMPLE 12

5.16 g of propargyl n-butyl cinnamate ester (0.02 mole), 7.28 g of a hydrogenmethyl/dimethyl siloxane polysiloxane copolymer having an average formula of

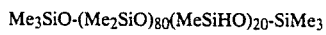

(0.02 mole) and 25 ml of toluene were added to a flask equipped with a condenser, thermometer probe, stirrer and nitrogen blanket. The mixture was heated to 92° C. when 66 mg of a platinum containing complex were added. The reaction mixture was allowed to reflux for approximately 2½ hours and then allowed to cool. After evaporation of the solvent an oil was obtained which was washed with 3×25 ml of methanol. Analysis showed a 99% reaction yielding a product of the general formula $Me_3SiO(Me_2SiO)_{80}(MeSiO)_{20}SiMe_3$

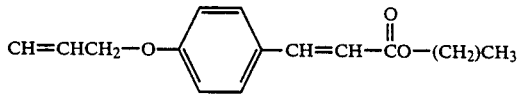

UV ABSORPTION TESTS

Products of Examples 6-11 were tested for their UV-absorption. Samples A-G, which were prepared as described below, were irradiated with a medium pressure Hg lamp of 250 W, 200–250 V. A UV filter was made from a solution of CoCl$_2$.H$_2$O in MeOH (10% W/V) and had a path length of 1 cm. This absorbed wavelength below 254 nm. The reaction cell and the filter were mounted onto an optical bench fitted with a collimator and a lens. The samples A–F were prepared by making a concentration of the products of Examples 6–11 respectively in hexane so as to give an initial absorbance of about 2.00. Sample G was prepared for comparative testing using a commercially used sunscreen agent Parsol MCX, provided by Givaudan. The UV absorbance was followed over a period of about 3–4 hours and the results are shown in Table II.

TABLE II

| Sample | % Absorbance with Time (Minutes) | | | | | |
|---|---|---|---|---|---|---|
| | 0 | 30 | 60 | 90 | 120 | 180 |
| A | 100 | 37 | 26 | 23 | 20 | 20 |
| B | 100 | 73 | 70 | 65 | 63 | 55 |
| C | 100 | 75 | 71 | 67 | 65 | 58 |
| D | 100 | 76 | 74 | 73 | 72 | 71 |
| E | 100 | 82 | 79 | 78 | 77 | 75 |
| F | 100 | 82 | 81 | 81 | 81 | 81 |
| G | 100 | 83 | 83 | 81 | 80 | 80 |

As can be seen from the results of the UV absorbance tests, the organosiloxanes having chromophore substituents on the terminal siloxane units (Samples B–F) show a better resistance to degradation under the influence of the radiation than those which are copolymers having pendant chromophore groups in the siloxane chain (Sample A). Of those having such groups in terminal positions, those having longer chain lengths (Samples D–F) are more efficient and match quite well with the stability of the cinnamate sunscreening agent by itself (Sample G).

That which is claimed is:

1. An organosilicon compound having at least one unit of the general formula

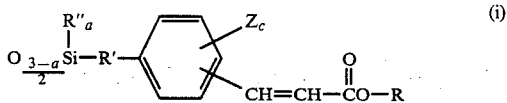

(i)

any other units present in the said organosilicon compound being represented by the general formula

(ii)

in which general formulae R represents an alkyl group having up to about 18 carbon atoms, R' is selected from the group consisting of divalent alkylene, oxyalkylene, alkenylene and oxyalkenylene groups having from 2 to 20 carbon atoms, wherein the carbon-carbon double bond of the alkenylene and oxyalkenylene group is adjacent to the silicon atom, R" is selected from the group consisting of halogen atoms and alkyl, aryl, alkoxy and alkoxyalkoxy groups having less than 9 carbon atoms, Q is selected from the group consisting of hydrogen, monovalent hydrocarbon and halogenated hydrocarbon groups having less than 19 carbon atoms, Z is selected from the group consisting of alkyl and alkoxy groups having from 1 to 8 carbon atoms and hydroxyl groups, a and b are integers with a value from 0 to 3 and c is an integer selected from 0 and 1, and wherein at least one of Z and R' is linked to the multivalent aryl group via an ether linkage.

2. An organosilicon compound according to claim 1 wherein a is an integer with a value from 0 to 2 and a maximum of 20% of all units are units of the general formula (i).

3. An organosilicon compound according to claim 1 wherein the units of the general formula (i) are only present as terminal units of the organosilicon compound.

4. An organosilicon compound according to claim 1 wherein the unit (i) is selected from the general formulae

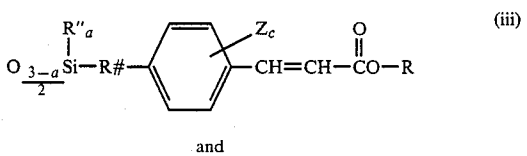

(iii)

and

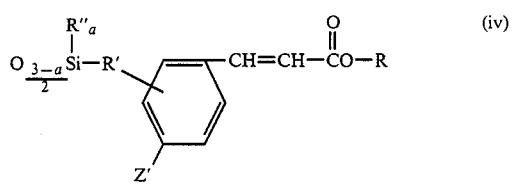

(iv)

wherein R, R', R", Z, a and c are as defined above, R$^\#$ is selected from the group consisting of divalent oxyalkylene and oxyalkenylene groups having from 2 to 20 carbon atoms linked to —(C$_6$H$_{4-c}$)— via the oxygen atom, the carbon-carbon double bond, if present, being adjacent to the silicon atom and Z' is selected from the group consisting of hydroxyl and alkoxy groups having from 1 to 8 carbon atoms.

5. An organosilicon compound according to claim 1 which is a substantially linear organosiloxane polymer wherein at least 80% of all R" and Q groups are methyl groups.

6. An organosilicon compound according to claim 1 wherein R' has 3 to 4 carbon atoms and wherein Z is selected from methoxy and ethoxy.

7. An organosilicon compound according to claim 4 wherein R' or R$^\#$ have 3 to 4 carbon atoms and wherein Z and Z' are selected from methoxy and ethoxy.

8. An organosilicon compound according to claim 1 which has a maximum absorbance at 300–320 nm.

9. An organosilicon compound according to claim 1 which has a total of at least 100 units, each unit selected from those of the general formulae (i) and (ii).

* * * * *